US009873119B2

(12) United States Patent
Eshoo et al.

(10) Patent No.: US 9,873,119 B2
(45) Date of Patent: Jan. 23, 2018

(54) MULTIPLE-ANALYTE ASSAY DEVICE AND SYSTEM

(71) Applicant: IBIS BIOSCIENCES, INC., Carlsbad, CA (US)

(72) Inventors: Mark W. Eshoo, San Diego, CA (US); John Picuri, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 154 days.

(21) Appl. No.: 14/369,632

(22) PCT Filed: Dec. 28, 2012

(86) PCT No.: PCT/US2012/072091
§ 371 (c)(1),
(2) Date: Jun. 27, 2014

(87) PCT Pub. No.: WO2013/102093
PCT Pub. Date: Jul. 4, 2013

(65) Prior Publication Data
US 2015/0010900 A1 Jan. 8, 2015

Related U.S. Application Data

(60) Provisional application No. 61/580,920, filed on Dec. 28, 2011.

(51) Int. Cl.
*B01L 3/00* (2006.01)
*G01N 33/543* (2006.01)
*B01L 7/00* (2006.01)
*G01N 35/00* (2006.01)

(52) U.S. Cl.
CPC .......... *B01L 3/502769* (2013.01); *B01L 7/00* (2013.01); *G01N 33/54366* (2013.01); *B01L 2200/06* (2013.01); *B01L 2200/10* (2013.01); *G01N 2035/00158* (2013.01)

(58) Field of Classification Search
CPC ................... B01L 3/502769; G01N 33/54366
See application file for complete search history.

(56) References Cited

U.S. PATENT DOCUMENTS

| | | |
|---|---|---|
| 4,613,422 A | 9/1986 | Lauks |
| 4,739,380 A | 4/1988 | Lauks et al. |
| 4,933,048 A | 6/1990 | Lauks |
| 5,063,081 A | 11/1991 | Cozzette et al. |
| 5,096,669 A | 3/1992 | Lauks et al. |
| 5,200,051 A | 4/1993 | Cozzette et al. |
| 5,447,440 A | 9/1995 | Davis et al. |
| 5,628,961 A | 5/1997 | Davis et al. |
| 5,821,399 A | 10/1998 | Zelin |
| 5,837,446 A | 11/1998 | Cozzette et al. |

(Continued)

OTHER PUBLICATIONS

International Search Report and Written Opinion for Application No. PCT/US2012/072091, dated Mar. 13, 2013, 12 pages.

(Continued)

*Primary Examiner* — Melanie Yu Brown
(74) *Attorney, Agent, or Firm* — Casimir Jones, S.C.

(57) ABSTRACT

Provided herein are systems and methods for performing complex chemical, physical and biological assays. In particular, provided herein are systems and methods for performing microfluidic assays.

16 Claims, 2 Drawing Sheets

(56) References Cited

U.S. PATENT DOCUMENTS

| | | |
|---|---|---|
| 5,837,454 A | 11/1998 | Cozzette et al. |
| 6,030,827 A | 2/2000 | Davis et al. |
| 6,300,138 B1 * | 10/2001 | Gleason .............. B01L 3/50273 422/547 |
| 6,379,883 B2 | 4/2002 | Davis et al. |
| 6,750,053 B1 | 6/2004 | Widrig et al. |
| 7,381,374 B2 * | 6/2008 | Tsai ..................... B01L 3/5027 422/554 |
| 7,419,821 B2 | 9/2008 | Davis et al. |
| 7,540,948 B2 | 6/2009 | Collier et al. |
| 7,723,099 B2 | 5/2010 | Miller et al. |
| 2002/0071788 A1 * | 6/2002 | Fujii ................... B01L 3/50273 422/400 |
| 2002/0123059 A1 * | 9/2002 | Ho ........................ B01L 3/5027 435/6.11 |
| 2003/0170881 A1 | 9/2003 | Davis et al. |
| 2006/0257993 A1 | 11/2006 | McDevitt et al. |
| 2007/0098600 A1 * | 5/2007 | Kayyem .............. B01L 3/5027 422/400 |
| 2007/0166195 A1 * | 7/2007 | Padmanabhan ... B01L 3/502715 422/68.1 |
| 2010/0028984 A1 | 2/2010 | Duong et al. |

OTHER PUBLICATIONS

Lowe C.R., "Biosensors," Trends in Biotechnology, 1984, vol. 2 (3), pp. 59-65.

\* cited by examiner

MULTIPLE-ANALYTE ASSAY DEVICE AND SYSTEM

CROSS-REFERENCE TO RELATED APPLICATIONS

The present Application claims priority to U.S. Provisional Application Ser. No. 61/580,920 filed Dec. 28, 2011, the entirety of which is incorporated by reference herein.

STATEMENT REGARDING FEDERALLY SPONSORED RESEARCH OR DEVELOPMENT

This invention was made with government support under HDTRA1-10-C-0081 awarded by the Defense Threat Reduction Agency. The government has certain rights in the invention.

FIELD OF INVENTION

Provided herein are systems and methods for performing complex chemical, physical and biological assays. In particular, provided herein are systems and methods for performing microfluidic assays.

BACKGROUND

Numerous laboratory tests for analytes of interest are performed on biological or environmental samples for diagnosis, screening, disease staging, forensic analysis, pregnancy testing, drug testing, and other reasons. However, most of these quantitative tests require the expertise of trained technicians in a laboratory setting using sophisticated instruments. Moreover, laboratory testing increases the cost of analysis and delays the results. It would be advantageous to perform such analyses at the point of care, accurately, inexpensively, and with a minimum of delay.

Some solutions to this problem have been developed, for example, using a disposable cartridge configured to analyze a single analyte and a portable, hand-held reading apparatus configured to accept the cartridge, process the data, and present data to a user (see, e.g., U.S. Pat. Nos. 7,419,821 and 5,096,669, herein incorporated by reference in their entireties). These cartridges have a single input and a single output for communicating with the reader, e.g., to transmit and receive signals for controlling the analysis and transferring the resulting data. However, many molecular tests require (or would benefit from) assessing the presence or absence of, or measuring the amount or concentration of, multiple analytes.

Accordingly, the field has a need for a testing technology that provides point-of-care, real-time testing of analytes.

SUMMARY

Provided herein are systems and methods for performing complex chemical, physical and biological assays. In particular, provided herein are systems and methods for performing microfluidic assays.

Embodiments of the present invention provides system and methods that utilize fluidic devices with rational arrangements of reagent vessels around a central reaction vessel. The devices provide the advantages of being able to perform multi-step or multiple reaction assays without transferring sample from the central reaction vessel. Advantage of the devices of embodiments of the present invention relative to traditional fluidics designs is exemplified in FIG. 1.

For example, in some embodiments, the present invention provides a device for performing an assay, comprising: a) a central reaction vessel; and b) a plurality (e.g., two or more, 3 or more, 4 or more, 5 or more, 6 or more, 8 or more, 10 or more, etc.) of auxiliary vessels in direct fluid communication with the reaction vessel, wherein the auxiliary vessels are in a radial arrangement around the central reaction vessel. In some embodiments the device further comprises one or more sample input and/or output components in fluid communication with the central reaction vessel. In some embodiments, the auxiliary vessels comprise reagents for performing one or more assays. In some embodiments, the assay detects an analyte. In some embodiments, the assay is, for example, an enzymatic assay, a chemical assay, a biochemical assay, a physical assay or a biological assay. One of skill in the art recognizes that additional assays may be performed using the devices and systems described herein. In some embodiments, the analyte is, for example, of a chemical, a nucleic acid, a polypeptide, a lipid, a carbohydrate, a metabolite, a toxin, a cell, a pathogen, etc. or combinations thereof.

In further embodiments, the present invention provides a system, comprising: a) one or more of the devices described herein; and b) an external source of environmental control (e.g., heater/cooler, light source, ultrasonic transducer, etc.). In some embodiments, the system further comprises a plurality of sample preparation components in fluid communication with the device. In some embodiments, the sample preparation components are, for example, cell lysis components, nucleic acid extraction components, sample purification components or analyte capture components. In some embodiments, the system further comprises a plurality of sample detection or analysis components. In some embodiments, the sample detection or analysis components comprise sensors. In some embodiments, the system is configured as a cartridge.

Additional embodiments of the present invention provide a method of performing an assay, comprising: a) contacting a sample with a system as described herein; and b) performing an assay with the system. In some embodiments, the assay is, for example, an enzymatic assay, a chemical assay, a biochemical assay, an immunological assay, a physical assay or a biological assay. In some embodiments, the analyte is, for example, a chemical, a nucleic acid, a polypeptide, a lipid, a carbohydrate, or combinations thereof.

In some embodiments, the method comprises detecting the presence of absence of an analyte in the sample using the system. In some embodiments, the sample is, for example, a biological sample, an environmental sample, a cellular sample (e.g., of a virus, a bacteria, a fungi, or a eukaryotic cell), or a chemical sample.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

DETAILED DESCRIPTION

Figure 1:
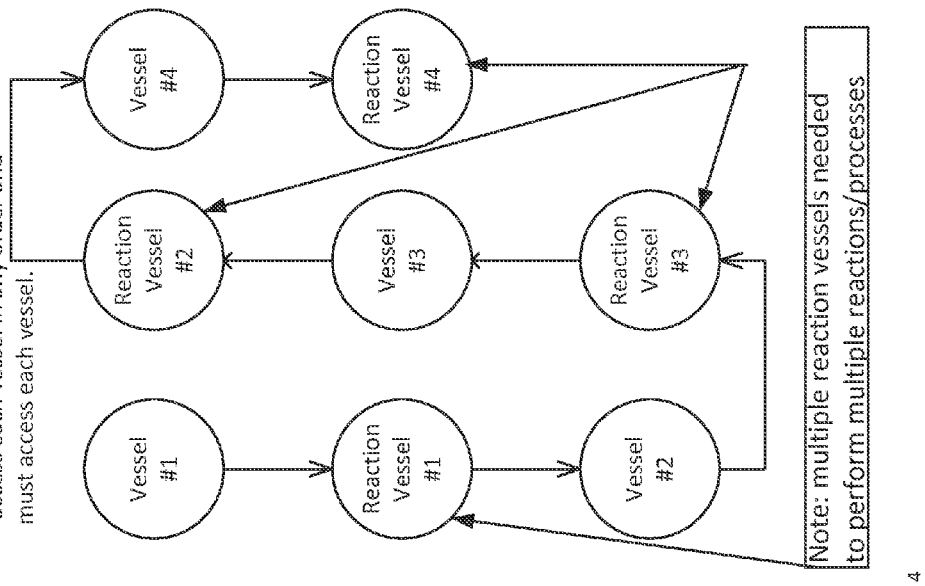
FIG. 1 shows a comparison of the radial architecture of embodiments of the present invention with traditional linear architecture.
Figure 1:
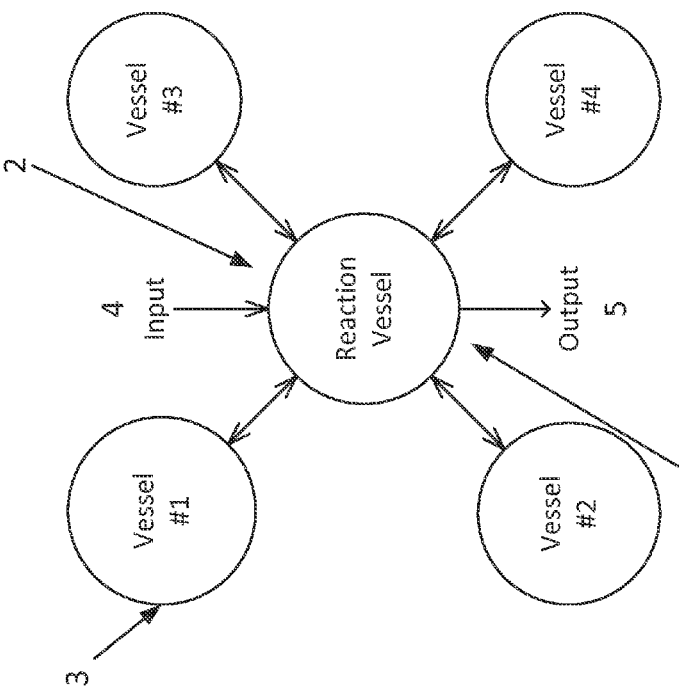

Provided herein are systems and methods for performing complex chemical, physical and biological assays. In particular, provided herein are systems and methods for performing microfluidic assays.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, a "signal" is a time-varying quantity associated with one or more properties of a sample that is assayed. A signal can be continuous in the time domain or discrete in the time domain. As a mathematical abstraction, the domain of a continuous-time signal is the set of real numbers (or an interval thereof) and the domain of a discrete-time signal is the set of integers (or an interval thereof). Discrete signals often arise via "digital sampling" of continuous signals. For example, an audio signal consists of a continually fluctuating voltage on a line that can be digitized by reading the voltage level on the line at a regular interval, e.g., every 50 microseconds. The resulting stream of numbers is stored as a discrete-time digital signal.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Environmental samples include environmental material such as surface matter, soil, mud, sludge, biofilms, water, and industrial samples. Such examples are not however to be construed as limiting the sample types applicable to the present invention.

As used herein, the term "analyte" is to be construed broadly as any compound, molecule, or other substance of interest to be detected, identified, or characterized.

As used herein, the term "sensor" refers to an ambient sensing device such as, for example, ion sensitive and chemical sensitive devices that generate an electrical signal (e.g., current, potential, or conductivity) based on the presence of or concentration of an analyte in the sample being tested.

Embodiments Of The Technology

Although the disclosure herein refers to certain illustrated embodiments, it is to be understood that these embodiments are presented by way of example and not by way of limitation.

Embodiments of the present invention provide system and methods for performing complex multistep physical, chemical and biochemical assays using a simple to manufacture but versatile fluidic architecture. In some embodiments, the fluidics is microfluidics. In some embodiments, the present invention provides a device comprising a central reaction vessel linked radially to other auxiliary vessels that perform other functions such as reagent addition, sonication, etc. The use of the central reaction vessel allows for a number of reactions each needing specific external inputs (e.g., reagents, temperature, light, sonic energy, etc.) to be performed in series with only one external source (e.g., a heater/cooler (e.g., thermo electric heater/cooler), light source, ultrasonic transducer, etc.). The radial nature of the architecture also makes it modular and versatile as each node can be accessed in any order (or not at all) and allows for any combination of processes (e.g., such as reagent additions or analysis) to be carried out. This allows for a single architecture to be used for multiple different workflows reducing the upfront manufacturing costs of systems (e.g., cartridges) and allowing for a single controller unit to run an assortment of workflows.

Other architectures proceed in a linear fashion moving from a reaction vessel to a vessel to perform another function (such as adding a reagent, performing sonication, etc.) then onto a second reaction vessel repeating this cycle all the way through the process. This linear flow makes the architecture less versatile as each workflow needs its own unique layout. Additionally, zones with external inputs such as thermo-electic heating/cooling, ultrasonic transducers, light sources, etc. must either be repeated many times to accommodate all the necessary inputs or the fluid path must be re-routed over shared inputs (which also might need to be made larger than originally needed to accommodate the multiple fluid paths). Either of these options adds complexity to the process either by adding complexity/cost to the controller box or adding complexity/cost to the cartridge.

The devices, systems and methods described herein allows for a much simpler design of both the cartridge and controller unit as compared to the commonly used linear architecture. As one reaction vessel and its associated external input can be used repeatedly, there is not the same need as the linear architecture to add complexity to the controller device by adding multiple input devices nor is there the need to add complexity to the cartridge by re-routing fluid over the same input repeatedly. Additionally, unlike the linear architecture, the radial architecture is much more modular allowing for a single cartridge design and/or controller unit to accommodate multiple different workflows.

The devices, systems and methods described herein find use in a variety of applications including, but not limited to, chemical, biochemical and physical processes such as immunoassays, library preparation for next generation sequencing, PCR based diagnostics, etc.

1. Devices

In some embodiments, the present invention provides devices and systems for performing assays. FIG. 1 (left panel) provides an overview of exemplary radial assay devices 1 of embodiments of the present invention. In some embodiments, the device 1 comprises a central reaction vessel 2 and one or more (e.g., two or more, 3 or more, 4 or more, 5 or more, 6 or more, 8 or more, 10 or more, etc.) auxiliary vessels 3 (e.g., for providing assay reagents). In some embodiments, the device comprises input 4 and output 5 access (e.g., channels for introducing and removing sample).

In some embodiments, devices are designed as a disposable cartridge for performing assays on samples. Embodiments of the cartridges take many forms and configurations and they are constructed from many suitable materials. For example, U.S. Pat. No. 7,419,821, incorporated herein in its entirety for all purposes, provides an example of a single-use cartridge. Furthermore, a disposable sensing device for measuring analytes in a blood sample is disclosed in U.S. Pat. Nos. 5,096,669; 6,750,053; 7,723,099. Other devices are disclosed in U.S. Pat. Nos. 5,628,961 and 5,447,440 for measuring clotting time.

In some embodiments, the cartridges are used with a single sample. The use of such cartridges provides a convenient way to test samples while minimizing sample contamination and sample carry-over risks. Appropriately, in some embodiments, the cartridges are disposable.

In some embodiments, devices comprise an apparatus for reading results of an assay. Moreover, in some embodiments a processor is configured to control the reading apparatus. In some embodiments, the processor is used to initiate and/or terminate the measurement and data collection. In some embodiments, the device comprises a user interface (e.g., a keyboard, buttons, dials, switches, and the like) for receiving user input that is used by the processor to direct a measurement. In some embodiments, the device further comprises a data output for transmitting (e.g., by a wired or wireless connection) data to an external destination, e.g., a computer, a display, a network, and/or an external storage medium. Some embodiments provide that the device is a small, handheld, portable device incorporating these features and components. Examples of a reading apparatus are provided in U.S. Pat. Nos. 5,096,669 and 5,821,399, which are both hereby incorporated by reference in their respective entireties for all purposes.

In some embodiments, devices are provided as part of a kit or system comprising reagent and components necessary, sufficient or useful for performing assays. For example, in some embodiments, systems include sample prep components 6 for purification or capture of nucleic acids or proteins from samples (e.g., biological samples) as well as analysis components. In some embodiments, systems comprise a plurality of radial reaction devices with components for different types of analysis.

Figure 2:
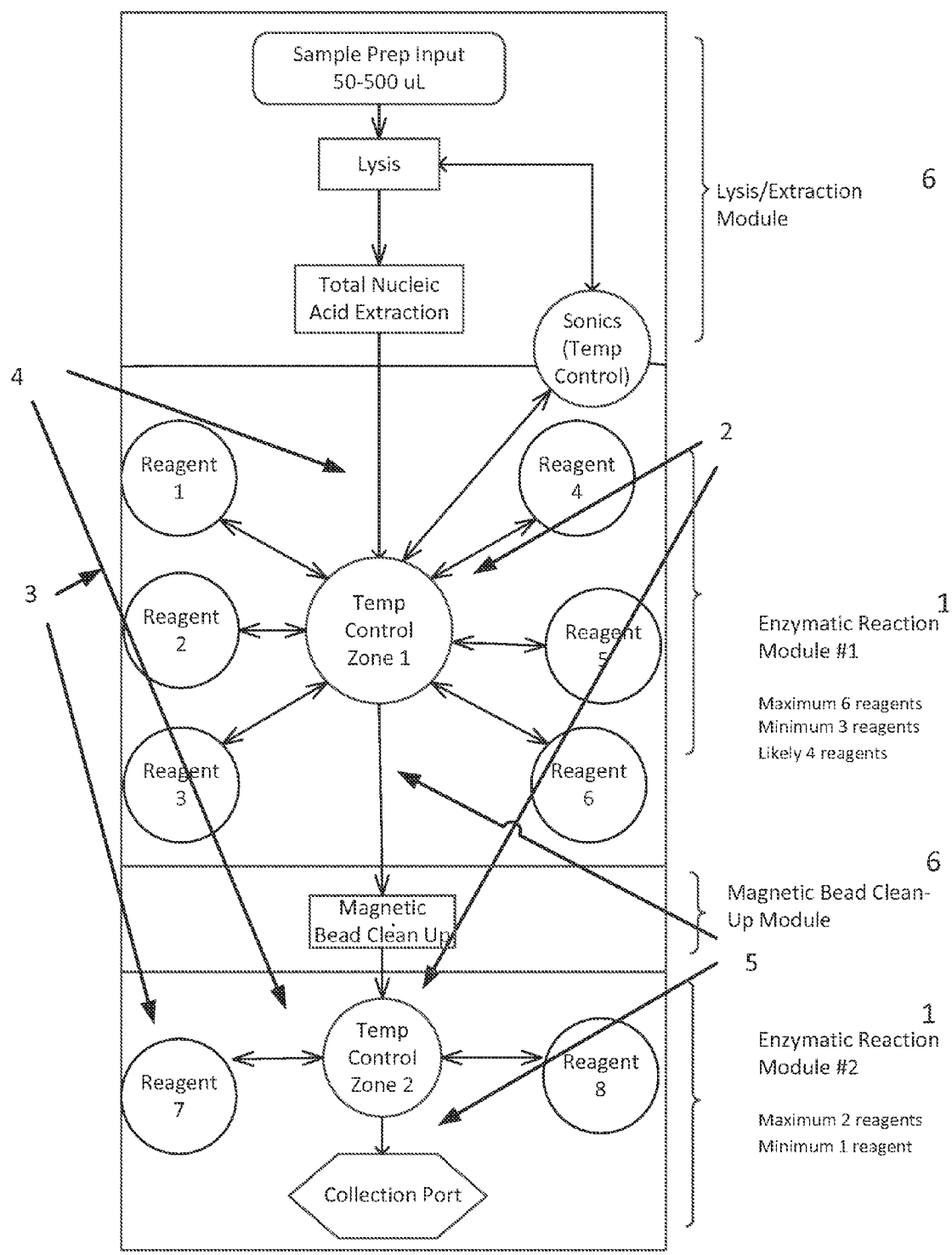
FIG. 2 shows a schematic of a cartridge of embodiments of the present invention.

FIG. 2 shows an exemplary system of embodiments of the present invention. The purification and analysis of nucleic acids is one exemplary embodiments of the present invention. One of ordinary skill in the art understands that the devices and systems described herein find use in a variety of applications in multiple scientific fields.

FIG. 2 shows the use of a device of embodiments of the present invention in a cartridge format for purification and analysis of nucleic acids. A sample (e.g., a biological sample comprising nucleic acids) is input into a lysis/extraction module 6 where any cells are lysed and nucleic acids are purified from the cells. Sample (e.g., nucleic acid) is then transferred to a first central reaction vessel 2 for analysis (e.g., enzymatic reaction). The sample is then transferred via sample output component 5 to a further sample prep module 6 (e.g., for capture or further purification) or a second reaction vessel 6 for further analysis. Following analysis, sample is optionally transferred a via output component 5 to a collection port (e.g., for analysis).

In some embodiments, systems further comprise sensors (e.g., for detecting the presence or a property of sample that has been processed/analyzed using the devices described herein). While not limited in the types of sensors that may be used, it is contemplated that the systems described herein comprises microfabricated sensors suitable for mass production and capable of detecting a wide range of biological molecules. Examples of such electrochemical analyte sensors are provided in U.S. Pat. Nos. 4,613,422; 4,739,380; 4,933,048; 5,063,081; 5,200,051; 5,837,446; 5,837,454; 6,030,827; 6,379,883; 7,540,948; including reference sensors in U.S. Pat. No. 7,723,099, all of which are incorporated herein by reference in their entireties for all purposes. Other sensors and detectors may be utilized herein (e.g., spectrometry, spectrophotometry, chemical, immunological and the like).

In particular embodiments of the present invention, the transduction of the analyte concentration into a processable signal is by an electrochemical means. These transducers may include amperometric, potentiometric (voltammetric), or conductimetric sensors. However, the technology may comprise other types of transducers (e.g., acoustic wave sensing devices, thermistors, gas-sensing electrodes, field-effect transistors, optical and evanescent field wave guides, and the like). A useful discussion and tabulation of transducers which may be used in a sensor as well as the kinds of analytical applications in which each type of transducer or sensor, in general, may be utilized is found in Trends in Biotech. 2(3): 59-65 (1984), the disclosures and descriptions contained therein are incorporated by reference herein for all purposes. Of the three electroanalytical techniques mentioned earlier, the potentiometric and amperometric techniques are preferred because the output signal may most easily be related directly to the response of the sensor to a particular analyte.

In some embodiments the electrochemical analyte sensor is used to detect and/or quantify an immunoactive analyte. The analysis scheme for the detection of low concentrations of an immunoactive analyte relies on the formation of an enzyme-labeled antibody/analyte/surface-bound antibody "sandwich" complex. The concentration of analyte in a sample is converted into a proportional surface concentration of an enzyme. The enzyme is capable of amplifying the analyte's chemical signal by converting a substrate to a detectable product. For example, where alkaline phosphatase is the enzyme, a single enzyme molecule can produce several thousand detectable molecules per minute, improving by several orders of magnitude the detectability of the analyte compared to schemes in which a detectable species is attached to the antibody in place of alkaline phosphatase.

In some embodiments of this detection technology, the sensors detect an electrogenic species. The electrogenic species is a chemical, moiety, or composition that is not electroactive until an enzyme converts it into an electroactive species. The inactive species is provided in the sample reaction mixture and conversion to the active form is associated with, and thus indicative of, a property of the analyte (e.g., concentration, conformation, amount, oligomerization state, binding state, etc.). For example, in some embodiments the electrogenic species is a ferrocene derivative, p-aminophenol, hydrogen peroxide, and/or ammonium ion. It is to be understood that these examples are demonstrative and the technology is not limited in the electrogenic species that finds use in the sensor. Furthermore, in some embodiments an enzyme produces the electrogenic species. Examples of enzymes that produce electrogenic species include, but are not limited to, alkaline phosphatase, glucose oxidase, lactate oxidase, glutamate oxidase, choline oxidase, cholesterol oxidase, alcohol oxidase, amyloglucosidase oxidase, lysine oxidase, L-amino acid oxidase, ascorbate oxidase, galactose oxidase, and urease. In some embodiments, the electrogenic species is derived from an enzyme reaction associated with nucleotide capture.

In immunosensor embodiments, it is advantageous to contact the sensor first with a sample and then with a wash fluid prior to recording a response from the sensor. In specific embodiments, the sample is appended with an antibody-enzyme conjugate that binds to the analyte of interest within the sample before the amended sample contacts the sensor. Binding reactions in the sample produce an analyte/antibody-enzyme complex. The sensor comprises an immobilized antibody to the analyte, attached close to an electrode surface. Upon contacting the sensor, the analyte/antibody-enzyme complex binds to the immobilized antibody near the electrode surface. It is advantageous at this point to remove from the vicinity of the electrode as much of the unbound antibody-enzyme conjugate as possible to minimize background signal from the sensor. The enzyme of the antibody-enzyme complex is advantageously capable of converting a substrate, provided in the fluid, to produce an electrochemically active species. This active species is produced close to the electrode and provides either a current from a redox reaction at the electrode when a suitable potential is applied (amperometric operation). Alternatively, if the electroactive species is an ion, it can be measured potentiometrically. In amperometric measurements the potential may either be fixed during the measurement or varied according to a predetermined waveform. For example, a triangular wave can be used to sweep the potential between limits, as is used in the well-known technique of cyclic voltammetry. Alternatively, digital techniques such as square waves can be used to improve sensitivity in the detection of the electroactive species adjacent to the electrode. From the current or voltage measurement, the amount or presence of the analyte in the sample is calculated. These and other analytical electrochemical methods are well known in the art.

In one aspect, the present invention utilizes a sensor comprising a capture element and/or a capture reagent. Such elements are molecules, moieties, substances, or compositions that preferentially (e.g., specifically and selectively) interact with a particular target sought to be isolated and purified. Any capture element having desired binding affinity and/or specificity to the analyte target can be used in the present technology. For example, the capture element can be a macromolecule such as a peptide, a protein (e.g., an antibody or receptor), an oligonucleotide, a nucleic acid, (e.g., nucleic acids capable of hybridizing with the target nucleic acids), vitamins, oligosaccharides, carbohydrates, lipids, or small molecules, or a complex thereof. As illustrative and non-limiting examples, an avidin target capture element may be used to isolate and purify targets comprising a biotin moiety, an antibody may be used to isolate and purify targets comprising the appropriate antigen or epitope, and an oligonucleotide may be used to isolate and purify a complementary oligonucleotide (e.g., a poly-dT oligonucleotide may be used to isolate and purify targets comprising a poly-A tail).

Any nucleic acids, including single-, double-, and triple-stranded nucleic acids, are contemplated as targets for capture (e.g., the product of an amplification reaction (e.g., PCR, RT-PCR, TMA, NASBA, and the like); a genome or genomic fragment; a restriction fragment; an RNA (e.g., a tRNA; an mRNA; a microRNA; an siRNA an rRNA); a chromosome; a plasmid; a viral genome; a primer; a gene). Many kinds of compositions and/or moieties serve as a capture element. For example, a biotin-labeled nucleic acid can be captured using an avidin capture element or a nucleic acid comprising a poly-A tail can be captured by a poly-dT capture element. In some embodiments, a nucleic acid serves as the capture element. Any nucleic acid, including single-, double-, and triple-stranded nucleic acids, that are capable of binding, or specifically binding, to the target can be used as the capture element in the present device. Examples of such nucleic acids include DNA, such as A-, B- or Z-form DNA, and RNA such as mRNA, tRNA and rRNA, aptamers, peptide nucleic acids, and other modifications to the sugar, phosphate, or nucleoside base. Thus, there are many strategies for capturing a target and accordingly many types of capture elements are known to those in the art. While not limited in the means by which a target nucleic acid can be captured, some embodiments of the technology provided herein comprise using an oligonucleotide that is complementary to the target and that thus captures the target by specifically and selectively hybridizing to the target nucleic acid. Other embodiments use other capture strategies, e.g., an antibody.

In addition, target capture elements comprise a functionality to localize, concentrate, aggregate, etc. the capture element and thus provide a way to isolate and purify the target when captured (e.g., bound, hybridized, etc.) to the capture element, e.g., when a target:capture element complex is formed. For example, in some embodiments the portion of the target capture element that interacts with the target (e.g., the oligonucleotide) is linked to a solid support (e.g., a bead, surface, resin, column). Often, the solid support allows the use of a mechanical means to isolate and purify the target:capture element complex from a heterogeneous solution.

Also contemplated are embodiments wherein the sensor is a light sensor (e.g., a photodetector). The light sensor detects light and produces an electrical signal (e.g., a potentiometric, amperometric, or conductimetric signal). The light is related to a property or characteristic of the analyte measured in the assay (e.g., concentration, pH, conformation, activity, binding state, redox state, oligomerization state, amount, etc.). The light detected is produced by a number of sources and processes. For example, some assays of an analyte produce light by fluorescence or luminescence (e.g., bioluminescence) and some assays comprise the use of a quantum dot and the quantum dot produces light. In some assays, the light is detected after passing through the sample (e.g., in an assay (e.g., a spectrophotometric assay) that measures the transmittance or absorbance of the sample).

The light sensor can be configured in any way that allows monitoring the optical properties of the sample and/or an analyte. For example, some embodiments provide that the sensor monitors light intensity. In embodiments used for spectrometry, the sensor detects light at a wavelength that is about the same wavelength as the wavelength that is incident on the sample and/or analyte. In fluorescence detection embodiments, the sensor monitors light intensity at a wavelength that is longer than the wavelength that is incident on the sample and/or analyte. The sensor comprises any suitable technology to measure optical properties. For example, in some embodiments the sensor is a spectrometer. Additional embodiments provide that the sensor is a photoresister, a photovoltaic cell, a photodiode, a photomultiplier tube, a photocathode, a phototransister, a charge-coupled device, or a reverse-biased LED. In some embodiments, the sensor monitors one or more wavelengths and in some embodiments the photodetector records a spectrum.

2. Uses

The systems and devices described herein are useful for the convenient and real-time detection, analysis, etc. of any number of diverse analyte species. For example, types or classes of analytes include, but are not limited to, chemicals, ionophores, ion exchangers, enzymes, biochemical metabolites, biological ions, respiratory gases, antibodies, antigens, lectins, neurochemical receptors, crystals, polypeptides, nucleic acids (e.g., oligonucleotides, polynucleotides, nucleotides, nucleosides, molecules of DNA, molecules of RNA), proteins, prions, toxins, peptides, sugars, lipids, steroids, salts, ions, glycoproteins, metalloproteins, cofactors, immunoglobulins, and other macromolecules of physiological significance including mixtures or active fragments or subunits thereof. An analyte may be present in an isolated form or in a complex with other substances. In addition, an analyte may be associated with a cell, a tissue, a microorganism (e.g., living, dead, or a lysate or other composition derived therefrom), a virus, or other biological material or composition derived therefrom. Accordingly, the analyte is useful in some embodiments, for example, in detecting the presence of a microorganism, a virus, or a particular cell type (e.g., a cancer cell, a tissue type) in a sample.

The technology is useful in the detection of viruses, for example, HIV, HTLV, adenoviruses, herpesviruses, poxviruses, parvoviruses, picorinoviruses, togaviruses, orthomyxoviruses, rhabdoviruses, retroviruses, and hepadnaviruses, among others. Also, the technology is useful in detecting the causative agents, or markers associated with, prion-related diseases such as scrapie, chronic wasting disease, and bovine spongiform encephalopathy.

The present technology is useful for the analysis of most liquid samples including undiluted biological samples such as whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. It should also be understood that solid or dessicated samples may be dissolved in an appropriate solvent to provide a liquid mixture suitable for analysis. Multiplex assays may include collections of similar analytes (e.g., different nucleic acid molecules from a range of different organisms) or different analytes (e.g., a nucleic acid with a peptide with a small molecule, etc.).

The devices, systems and methods provided herein finds use in the medical, clinical, and emergency medical fields. Accordingly, in some embodiments the device is used to assay biological samples. In such an assay, the biological sample comprises the analyte and measuring a property of the analyte is indicative of a state or a property of the sample and, in some embodiments, the subject from which the sample was taken. Some relevant samples include, but are not limited to, whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate, a tissue homogenate, a cell homogenate, or the like. For example, for a subject who has diabetes, the sample is a blood sample and the analyte to be measured is glucose (e.g., glucose concentration).

Furthermore, in some embodiments the sample comprises or is suspected to comprise a composition associated with bioterrorism, e.g., a biological and/or chemical agent. A biological agent is, or is derived from, a living, typically pathogenic, biological organism (e.g., a bacterium, a virus, a eukaryote such as a fungus or a parasite). In some embodiments the sample comprises a biological toxin or other substance derived from a biological source (e.g., a small molecule, a protein, a prion). Bioterrorism agents are, or are derived from, biological sources; thus, particular biological signatures can be used to detect them, e.g., nucleic acids, proteins, or other small molecules that identify the biological agent and that can be detected by an appropriate assay, e.g., by an electrochemical analyte sensor. For example, an electrochemical analyte sensor can be used to detect a PCR amplicon, a virulence factor (e.g., a gene or protein), a toxin or genes encoding the production of a toxin, and/or markers associated with drug resistance.

Biological agents, some of military importance include, but are not limited to, *Bacillus anthracis* (causative agent of anthrax); *Staphylococcus* spp.; *Brucella abortus, Brucella melitensis*, and *Brucella suis* (causative agents of brucellosis); *Vibrio cholerae* (causative agent of cholera); *Corynebacterium diphtheriae* (causative agent of diphtheria); *Cryptosporidium parvum; Shigella dysenteriae* and *Escherichia coli* (causative agents of dysentery); *Burkholderia mallei* (causative agent of glanders); *Listeria monocytogenes* (causative agent of listerosis); *Burkholderia pseudomallei* (causative agent of meliodosis); *Yersinia pestis* (causative agent of plague); *Francisella tularensis* (causative agent of tularemia); *Chlamydia psittaci* (causative agent of psittacosis); *Coxiella burtetii* (causative agent of Q fever); *Rickettsia rickettsii* (causative agent of Rocky Mountain spotted fever); *Rickettsia prowazekii* and *Rickettsia typhi* (causative agents of typhus); *Coccidioides immitis* (causative agent of coccidiomycosis); Eastern, Western, and Venezuelan equine encephalitis viruses (causative agents of Equine encephalitis); Japanese encephalitis virus (causative agent of Japanese encephalitis); Rift Valley Fever virus (causative agent of Rift Valley fever); Variola virus (causative agent of smallpox); Yellow fever virus (causative agent of yellow fever); arenavirus (causative agent of Lassa fever and the Argentine, Bolivian, Brazilian, and Venezuelan hemorrhagic fevers); other viruses causative of hemorrhagic fevers; other viruses causative of viral encephalitis; Marburg virus; Ebola virus; Nipad virus; hantavirus; SARS; H1N1 influenza virus.

Furthermore, biological toxins with potential to be used as biological agents include, but are not limited to, ricin (derived from the castor bean *Ricinus communis*); saxitoxin (derived from a dinoflaggelate); staphylococcal entertoxin B (derived from *Staphylococcus aureus*); tetrodotoxin (derived from marine bacteria such as *Vibrio* species and *Pseudoalteromonas tetraodonis*); trichothecene mycotoxins (derived from fungi such as *Fusarium, Trichoderma*, and *Stachybotrys*); botulinum toxin (derived from *Clostridium botulinum*); epsilon toxin (derived from *Clostridium perfringens*); abrin toxin (derived from *Abrus precatorius*).

Along with smallpox, anthrax, plague, botulism, and tularemia, hemorrhagic fever viruses are among the six agents identified by the Centers for Disease Control and Prevention (CDC) as the most likely to be used as biological weapons. Hemorrhagic fever viruses include, but are not limited to, the arenaviridae (e.g., Lujo virus); the bunyaviridae (e.g., hantavirus); nairovirus (e.g., the Crimean-Congo hemorrhagic fever virus); *Phlebovirus* genus (Rift Valley fever virus); filoviridae (e.g., Ebola and Marburg viruses); and flaviviridae (e.g., dengue, yellow fever, Omsk hemorrhagic fever virus, and Kyasanur Forest disease virus).

While the technology finds use in detecting these and other agents in the context of bioterrorism, the technology is also used to detect the same and/or other agents in other contexts and applications. For example, the technology is useful to analyze samples from diseased patients or other subjects suspected of having a disease or having been exposed to a disease.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A system comprising:
   a) a cartridge comprising:
      i) a central reaction vessel; and
      ii) a plurality of auxiliary vessels radially linked in direct fluid communication with said central reaction vessel, wherein said auxiliary vessels comprise reagents for performing an assay, and wherein said assay detects an analyte without transferring said sample from said central reaction vessel; and
   b) an external source of environmental control in communication with said cartridge wherein said external source of environmental control is an ultrasonic transducer.

2. The system of claim 1, wherein said cartridge further comprises a sample input and/or a sample output component in fluid communication with said central reaction vessel.

3. The system of claim 1, wherein said assay is selected from the group consisting of an enzymatic assay, a chemical assay, a biochemical assay, an immunological assay, a physical assay, and a biological assay.

4. The system of claim 1, wherein said analyte is selected from the group consisting of a chemical, a nucleic acid, a polypeptide, a lipid, a carbohydrate, and combinations thereof.

5. The system of claim 1, wherein said external source of environmental control is selected from the group consisting of a heater/cooler, and a light source.

6. The system of claim 1, wherein said system further comprises a plurality of sample preparation components in fluid communication with said cartridge.

7. The system of claim 6, wherein said sample preparation components are selected from the group consisting of cell lysis components, nucleic acid extraction components, sample purification components, and analyte capture components.

8. The system of claim 1, wherein said system comprises a plurality of said cartridges.

9. The system of claim 1, wherein said system further comprises a plurality of sample detection or analysis components.

10. The system of claim 9, wherein said sample detection or analysis components comprise sensors.

11. A method of performing an assay, the method comprising:
    a) contacting a sample with the system of claim 1; and
    b) performing an assay with said system.

12. The method of claim 11, further comprising detecting the presence or absence of an analyte in said sample using one or more sample detection or analysis components.

13. The method of claim 11, wherein said assay is selected from the group consisting of an enzymatic assay, a chemical assay, a biochemical assay, a physical assay, and a biological assay.

14. The method of claim 12, wherein said analyte is selected from the group consisting of a chemical, a nucleic acid, a polypeptide, a lipid, a carbohydrate, and combinations thereof.

15. The method of claim 11, wherein said sample is selected from the group consisting of a biological sample, an environmental sample, a cellular sample, and chemical sample.

16. The method of claim 15, wherein said cellular sample comprises a virus, a bacterium, a fungus, and/or a eukaryotic cell.

* * * * *